United States Patent
Woods et al.

(10) Patent No.: US 9,835,568 B2
(45) Date of Patent: Dec. 5, 2017

(54) DEFECT CORRECTION USING TOMOGRAPHIC SCANNER FOR ADDITIVE MANUFACTURING

(71) Applicant: General Electric Company, Schenectady, NY (US)

(72) Inventors: Steven Charles Woods, Easley, SC (US); Tiffany Muller Craft, Simpsonville, SC (US); Kassy Moy Hart, Greenville, SC (US)

(73) Assignee: General Electric Company, Schenectady, NY (US)

( * ) Notice: Subject to any disclaimer, the term of this patent is extended or adjusted under 35 U.S.C. 154(b) by 116 days.

(21) Appl. No.: 15/096,608

(22) Filed: Apr. 12, 2016

(65) Prior Publication Data

US 2017/0292922 A1    Oct. 12, 2017

(51) Int. Cl.
| | |
|---|---|
| *B29C 35/08* | (2006.01) |
| *B29C 45/76* | (2006.01) |
| *B28B 11/00* | (2006.01) |
| *G01B 11/00* | (2006.01) |
| *G01N 23/04* | (2006.01) |

(52) U.S. Cl.
CPC ..... *G01N 23/046* (2013.01); *G01N 2223/335* (2013.01); *G01N 2223/646* (2013.01)

(58) Field of Classification Search
USPC .............. 264/40.1, 232, 236, 308, 401, 408; 118/712; 156/64, 272.8, 273.3
See application file for complete search history.

(56) References Cited

U.S. PATENT DOCUMENTS 5,141,677 A    8/1992   Fogarty
5,460,758 A *  10/1995  Langer ................. G03F 7/0037
                                                          118/429
(Continued)

FOREIGN PATENT DOCUMENTS

| DE | 102014226445 A1 * | 6/2016 | ......... B29C 67/0088 |
| EP | 1301140 B1 | 11/2010 | |
| WO | 2007147221 A1 | 12/2007 | |

OTHER PUBLICATIONS

English Abstract of DE 102014226445 (Year: 2017).*

(Continued)

*Primary Examiner* — Sing P Chan
(74) *Attorney, Agent, or Firm* — Ernest G. Cusick; Hoffman Warnick LLC

(57) ABSTRACT

A method for correction of thermal defects using tomographic scanning for additive manufacturing is provided. The method may include forming a portion of an object using an additive manufacturing system based on an intended three-dimensional (3D) model of the object that is in an additive manufacturing system format. The portion of the object is scanned using a tomographic scanner to obtain a model of the portion of the object in a tomographic scanner format. The model is converted from the tomographic scanner format into the additive manufacturing system format to obtain a converted tomographic model; and the converted tomographic model is compared to the intended 3D model to identify a defect in the portion of the object. A modified 3D model may be generated of the object correcting the intended 3D model to address the defect of the portion of the object.

16 Claims, 2 Drawing Sheets

(56) References Cited

U.S. PATENT DOCUMENTS

| | | | |
|---|---|---|---|
| 6,958,752 B2* | 10/2005 | Jennings, Jr. | G06T 19/20 345/419 |
| 7,087,200 B2 | 8/2006 | Taboos et al. | |
| 7,393,699 B2 | 7/2008 | Tran | |
| 7,625,198 B2* | 12/2009 | Lipson | A61L 27/36 425/169 |
| 7,651,506 B2 | 1/2010 | Bova et al. | |
| 7,710,415 B2* | 5/2010 | Jennings, Jr. | G06T 19/20 345/419 |
| 7,939,003 B2* | 5/2011 | Bonassar | A61L 27/36 101/491 |
| 8,048,359 B2 | 11/2011 | Wang et al. | |
| 8,636,938 B2* | 1/2014 | Bonassar | A61L 27/36 101/491 |
| 8,874,248 B2* | 10/2014 | Young | B29C 67/0088 345/419 |
| 8,877,112 B2* | 11/2014 | Bonassar | A61L 27/36 101/491 |
| 8,976,935 B2 | 3/2015 | Singh et al. | |
| 9,242,031 B2* | 1/2016 | Bonassar | A61L 27/36 |
| 9,420,260 B2* | 8/2016 | McGregor | G06T 19/20 |
| 9,492,968 B2* | 11/2016 | Wang | B22F 3/1055 |
| 2005/0078861 A1* | 4/2005 | Usikov | G06T 11/006 382/131 |
| 2006/0156978 A1* | 7/2006 | Lipson | A61L 27/36 118/708 |
| 2006/0160250 A1* | 7/2006 | Bonassar | A61L 27/36 438/1 |
| 2011/0169193 A1* | 7/2011 | Bonassar | A61L 27/36 264/308 |
| 2012/0133080 A1 | 5/2012 | Moussa et al. | |
| 2012/0155606 A1* | 6/2012 | Simon | G01N 23/046 378/19 |
| 2012/0232685 A1 | 9/2012 | Wang et al. | |
| 2013/0089642 A1* | 4/2013 | Lipson | A23P 20/20 426/115 |
| 2013/0166256 A1 | 6/2013 | Wirx-Speetjens et al. | |
| 2014/0052285 A1* | 2/2014 | Butcher | B29C 67/0051 700/98 |
| 2014/0117586 A1* | 5/2014 | Bonassar | A61L 27/36 264/401 |
| 2014/0379119 A1* | 12/2014 | Sciacchitano | G05B 19/4099 700/182 |
| 2015/0004046 A1* | 1/2015 | Graham | G06T 19/00 419/53 |
| 2015/0084238 A1* | 3/2015 | Bonassar | A61L 27/36 264/308 |
| 2015/0170013 A1* | 6/2015 | Wilson | G05B 19/188 235/468 |
| 2015/0170416 A1* | 6/2015 | McGregor | G06T 19/20 345/420 |
| 2015/0375456 A1 | 12/2015 | Cheverton et al. | |
| 2016/0066775 A1* | 3/2016 | Hunter | G01J 3/0291 600/178 |
| 2016/0095959 A1* | 4/2016 | Bonassar | A61L 27/36 264/308 |
| 2017/0053434 A1* | 2/2017 | McGregor | G06T 19/20 |

OTHER PUBLICATIONS

Pandey, Pulak M. and Raghunath, N.; "Improving Accuracy Through Shrinkage Modelling by Using Taguchi Method in Selective Laser Sintering"; Science Journal; Sep. 7, 2006; 12 pages; Elsevier, Science Direct, online publishing.

Ning, Y., Wong, Y. S., Fuh, J. Y. H. and H. T. Loh; "An Approach to Minimize Build Errors in Direct Metal Laser Sintering"; Science Journal; Jan. 2006; 8 pages; IEEE online publishing.

Nelson, Christian; McAlea, Kevin and Gray, Damien; "Imrovements in SLS Part Accuracy"; White paper; Date unknown; 12 pages; published by DTM Corporation; Austin, Texas.

Dai, K. and Shaw, L.; "Distortion Minimization of Laser-Processed Components Through Control of Laser Scanning Patterns"; Prototyping Journal; Nov. 5, 2002; 7 pages; vol. 8, No. 5; Emerald Group Publishing.

Yang, T.; Loh, H. T.; Fuh, J. Y. H.; Wong, Y. S.; Lu, L.; "Accuracy Analysis and Improvement for Direct Laser Sintering"; Research Journal; Nov. 4, 2003; 8 pages; published by the Department of Mechanical Engineering, National University of Singapore.

* cited by examiner

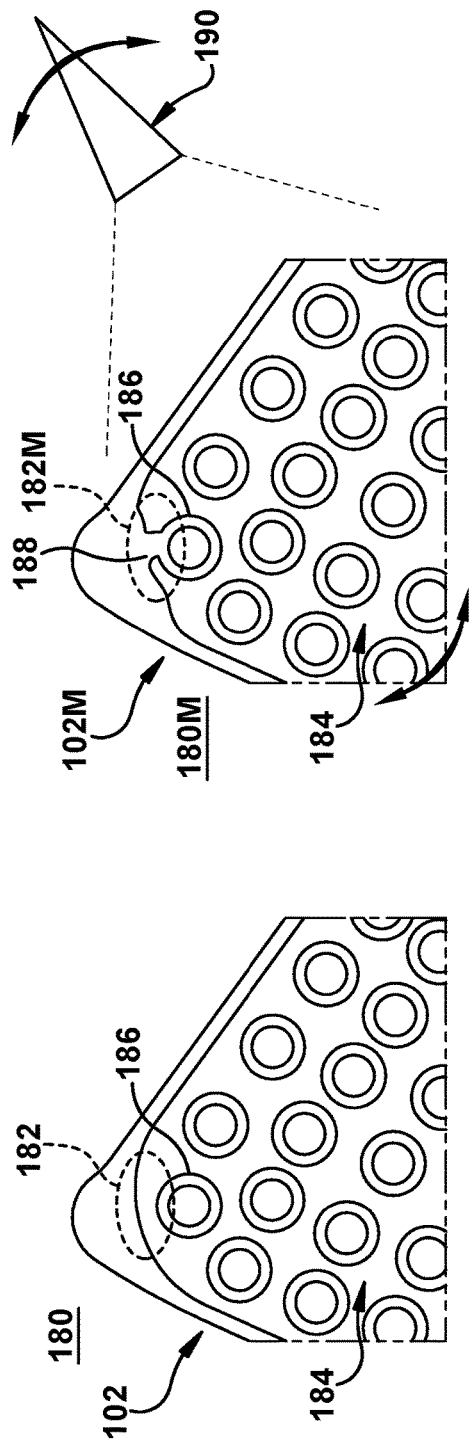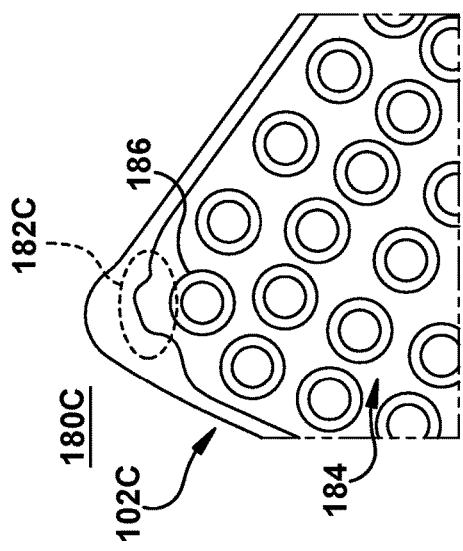

DEFECT CORRECTION USING TOMOGRAPHIC SCANNER FOR ADDITIVE MANUFACTURING

BACKGROUND OF THE INVENTION

The disclosure relates generally to additive manufacturing, and more particularly, to a method for correcting a three-dimensional model used for additive manufacturing based on defects identified using tomographic scanning.

Additive manufacturing (AM) includes a wide variety of processes of producing an object through the successive layering of material rather than the removal of material. As such, additive manufacturing can create complex geometries without the use of any sort of tools, molds or fixtures, and with little or no waste material. Instead of machining objects from solid billets of material, much of which is cut away and discarded, the only material used in additive manufacturing is what is required to shape the object.

Additive manufacturing techniques typically include taking a three-dimensional computer aided design (CAD) file of the object to be formed that includes an intended three-dimensional (3D) model or rendering of the object. The intended 3D model can be created in a CAD system, or the intended 3D model can be formulated from imaging (e.g., computed tomography (CT) scanning) of a prototype of an object to be used to make a copy of the object or used to make an ancillary object (e.g., mouth guard from teeth molding) by additive manufacturing. In any event, the intended 3D model is electronically sliced into layers, e.g., 18-102 micrometers thick, creating a file with a two-dimensional image of each layer. The file may then be loaded into a preparation software system that interprets the file such that the object can be built by different types of additive manufacturing systems. In 3D printing, rapid prototyping (RP), and direct digital manufacturing (DDM) forms of additive manufacturing, material layers are selectively dispensed to create the object.

In metal powder additive manufacturing techniques, such as selective laser melting (SLM) and direct metal laser melting (DMLM), metal powder layers are sequentially melted together to form the object. More specifically, fine metal powder layers are sequentially melted after being uniformly distributed using an applicator on a metal powder bed. The metal powder bed can be moved in a vertical axis. The process takes place in a processing chamber having a precisely controlled atmosphere of inert gas, e.g., argon or nitrogen. Once each layer is created, each two dimensional slice of the object geometry can be fused by selectively melting the metal powder. The melting may be performed by a high powered laser such as a 100 Watt ytterbium laser to fully weld (melt) the metal powder to form a solid metal. The laser moves in the X-Y direction using scanning mirrors, and has an intensity sufficient to fully weld (melt) the metal powder to form a solid metal. The metal powder bed is lowered for each subsequent two dimensional layer, and the process repeats until the three-dimensional object is completely formed.

In many additive manufacturing techniques, the layers are created following the instructions provided in the intended 3D model and use material either in a molten form or in a form that is caused to melt to create a melt pool. Each layer eventually cools to form a solid object. Imaging systems have been employed to ensure two-dimensional layers are formed accurately during additive manufacturing. However, one challenge with the cooling of the object is that a thermal defect can form in the object upon cooling, which prevents the object from conforming to the intended 3D model. The thermal defects typically cannot be identified during additive manufacturing because they are not present until later in the process. The thermal defects can also be difficult to identify after manufacturing because they are dimensionally very small and, oftentimes, are located in the object's interior. Current analysis techniques do not provide adequate mechanisms to identify the thermal defects and allow for corrections in the intended 3D model.

BRIEF DESCRIPTION OF THE INVENTION

A first aspect of the disclosure provides a method, comprising: forming a portion of an object using an additive manufacturing system based on an intended three-dimensional (3D) model of the object that is in an additive manufacturing system format; scanning the portion of the object using a tomographic scanner to obtain a scanner model of the portion of the object in a tomographic scanner format; converting the model from the tomographic scanner format into the additive manufacturing system format to obtain a converted tomographic model; comparing the converted tomographic model to the intended 3D model to identify a defect of the portion of the object; and generating a modified 3D model of the object correcting the intended 3D model to address the defect of the portion of the object.

A second aspect of the disclosure provides a method, comprising: forming a portion of an object using an additive manufacturing system based on an intended three-dimensional (3D) model of the object that is in an additive manufacturing system format; scanning the portion of the object using a computed tomography (CT) scanner to obtain a CT model of the portion of the object in a CT scanner format; converting the CT model from the CT scanner format into the additive manufacturing system format to obtain a converted CT model; comparing the converted CT model to the intended 3D model to identify a defect of the portion of the object; and generating a modified 3D model of the object correcting the intended 3D model to address the defect of the portion of the object.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIG. 2 shows a cross-sectional view through a selected plane of an intended three-dimensional (3D) model according to embodiments of the disclosure.

FIG. 3 shows a cross-sectional view through a selected plane of a three-dimensional (3D) tomographic scanner model of an object formed using additive manufacturing and including a thermal defect according to embodiments of the disclosure.

FIG. 4 shows a cross-sectional view through a selected plane of a three-dimensional (3D) model of an object, and including a correction to address the thermal defect in FIG. 3, according to embodiments of the disclosure.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

Figure 1:
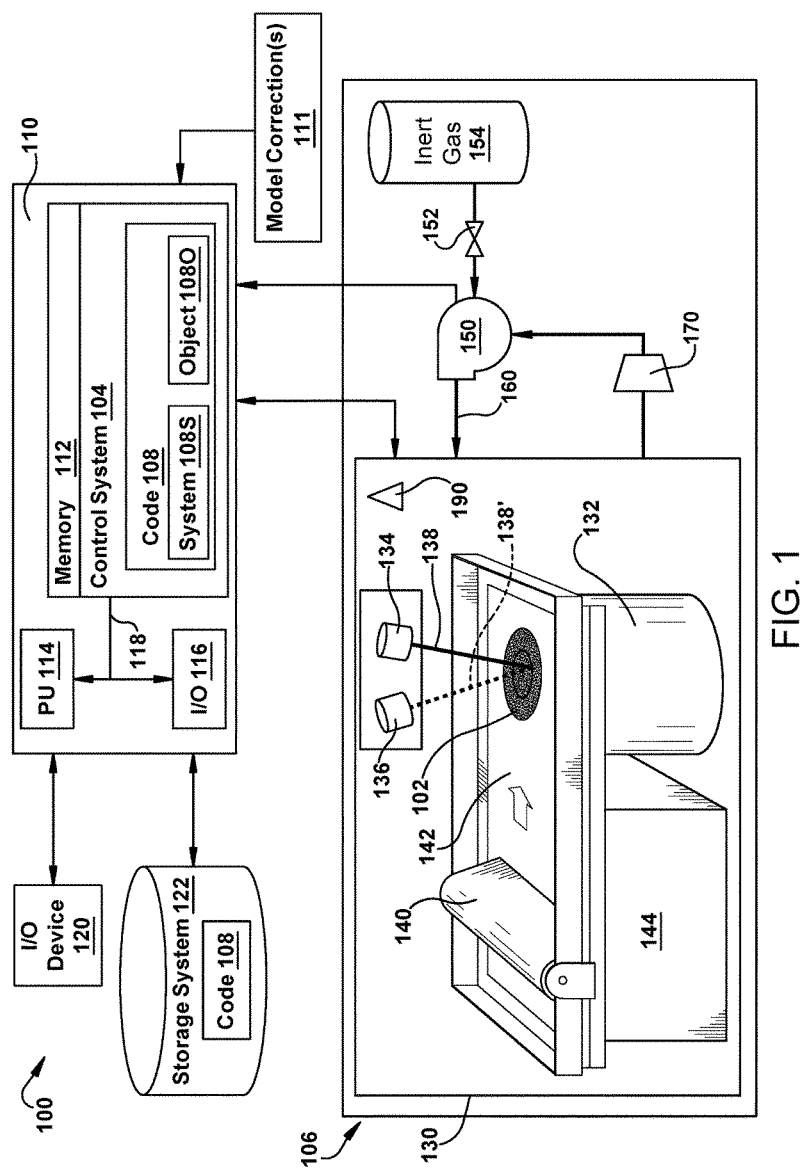
FIG. 1 shows a schematic block diagram of an additive manufacturing system including a reclamation system according to embodiments of the disclosure.

In the following specification and the claims, reference will be made to a number of terms, which shall be defined to have the following meanings:

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As indicated herein, the disclosure provides a method of identifying defects in an object created using additive manufacturing using tomographic scanning, and creating a correction for the intended 3D model to address the defect. As shown in FIG. 1, an object 102 may be formed by any additive manufacturing (AM) system 100 in which defects from cooling are a concern. As indicated, additive manufacturing may include any process of producing an object through the successive layering of material rather than the removal of material. Additive manufacturing can create complex geometries without the use of any sort of tools, molds or fixtures, and with little or no waste material. Instead of machining objects from solid billets of plastic, much of which is cut away and discarded, the only material used in additive manufacturing is what is required to shape the part. Additive manufacturing processes generally may include but are not limited to: 3D printing, rapid prototyping (RP), direct digital manufacturing (DDM), selective laser melting (SLM) and direct metal laser melting (DMLM). In terms of the current disclosure, additive manufacturing may include any process in which thermal defects are a concern. For purposes of description, DMLM has been chosen as the illustrative additive manufacturing process in which defects from cooling are a concern. It is emphasized that other additive manufacturing may present similar issues, and the teachings of the disclosure are not limited to any particular additive manufacturing process other than as stated herein.

FIG. 1 shows a schematic/block view of an illustrative computerized laser, metal powder additive manufacturing system 100 for generating an object 102, of which only an upper surface is shown. In this example, system 100 is arranged for direct metal laser melting (DMLM). It is understood that the general teachings of the disclosure are equally applicable to other forms of metal powder laser additive manufacturing such as those that may be referred to as selective laser melting (SLM). Object 102 is illustrated as a circular element; however, it is understood that the additive manufacturing process can be readily adapted to manufacture a large variety of parts.

System 100 generally includes a laser, metal powder additive manufacturing control system 104 ("control system") and an AM printer 106. As will be described, control system 104 executes code 108 to generate object 102 using multiple lasers 134, 136. Control system 104 is shown implemented on computer 110 as computer program code. To this extent, computer 110 is shown including a memory 112, a processor 114, an input/output (I/O) interface 116, and a bus 118. Further, computer 110 is shown in communication with an external I/O device/resource 120 and a storage system 122. In general, processor 114 executes computer program code 108 that is stored in memory 112 and/or storage system 122. While executing computer program code 108, processor 114 can read and/or write data to/from memory 112, storage system 122, I/O device 120 and/or AM printer 106. Bus 118 provides a communication link between each of the components in computer 110, and I/O device 120 can comprise any device that enables a user to interact with computer 110 (e.g., keyboard, pointing device, display, etc.). Computer 110 is only representative of various possible combinations of hardware and software. For example, processor 114 may comprise a single processing unit, or be distributed across one or more processing units in one or more locations, e.g., on a client and server. Similarly, memory 112 and/or storage system 122 may reside at one or more physical locations. Memory 112 and/or storage system 122 can comprise any combination of various types of non-transitory computer readable storage medium including magnetic media, optical media, random access memory (RAM), read only memory (ROM), etc. Computer 110 can comprise any type of computing device such as an industrial controller, a network server, a desktop computer, a laptop, a handheld device, etc.

As noted, system 100 and in particular control system 104 executes code 108 to generate object 102. Code 108 can include, inter alia, a set of computer-executable instructions ("printer") 108S for operating AM printer 106, and a set of computer-executable instructions ("object") 108O defining object 102 to be physically generated by AM printer 106. As described herein, additive manufacturing processes begin with a non-transitory computer readable storage medium (e.g., memory 112, storage system 122, etc.) storing computer-executable instructions code 108. Set of computer-executable instructions 108S for operating AM printer 106 may include any now known or later developed software code capable of operating AM printer 106.

Set of computer-executable instructions 108O defining object 102 may include a precisely defined, intended 3D model of object 102 and can be generated from any of a large variety of well-known computer aided design (CAD) software systems such as AutoCAD®, TurboCAD®, DesignCAD 3D Max, etc. In this regard, code 108O can initially include any now known or later developed file format. Furthermore, code 108O representative of object 102 may be translated between different file formats. For example, code 108O may include Standard Tessellation Language (STL) files which was created for stereolithography CAD programs of 3D Systems, or an additive manufacturing file (AMF), which is an American Society of Mechanical Engineers (ASME) standard that is an extensible markup-language (XML) based format designed to allow any CAD software to describe the shape and composition of any three-dimensional object to be fabricated on any AM printer. Code 108O representative of object 102 may also be converted into a set of data signals and transmitted, received as a set of data signals and converted to code, stored, etc., as necessary. In any event, code 108O may be an input to system 100 and may come from a part designer, an intellectual property (IP) provider, a design company, the operator or owner of system 100, or from other sources. In any event, control system 104 executes code 108S and 108O, dividing object 102 into a series of thin slices that it assembles using AM printer 106 in successive layers of material.

AM printer 106 may include a processing chamber 130 that is sealed to provide a controlled atmosphere for object 102 printing. A metal powder bed or platform 132, upon which object 102 is built, is positioned within processing chamber 130. A number of lasers 134, 136 are configured to melt layers of metal powder on metal powder bed 132 to generate object 102. While a pair of lasers 134, 136 will be described herein, it is emphasized that the teachings of the disclosure are applicable to a system employing only one or more than a pair of lasers 134, 136. Each laser 134, 136, as described relative to FIG. 1, has a field in which it can melt metal powder alone and an overlap region in which both lasers 134, 136 can melt metal powder. In this regard, each laser 134, 136 may generate laser beams 138, 138', respectively, that fuses particles for each slice, as defined by code 108. Laser 134 is shown creating a layer of object 102 using laser beam 138, while laser 136 is shown dormant but with a phantom laser beam 138'. Each laser 134, 136 is calibrated in any now known or later developed manner. That is, each laser 134, 136 has had its laser beam's anticipated position relative to platform 132 correlated with its actual position in order to provide an individual position correction (not shown) and alignment correction to ensure accuracy.

An applicator 140 may create a thin layer of raw material 142 spread out as the blank canvas from which each successive slice of the final object will be created. Various parts of AM printer 106 may move to accommodate the addition of each new layer, e.g., a metal powder bed 132 may lower and/or chamber 130 and/or applicator 140 may rise after each layer. The process may use different raw materials in the form of fine-grain metal powder or reactive metal powder, a stock of which may be held in a chamber 144 accessible by applicator 140. In the instant case, object 102 may be made of a "metal" which may include a pure metal or an alloy. The metal may include, for example, a reactive metal such as aluminum or titanium, or other reactive metals. System 100 is also capable of use with practically any non-reactive metal powder, i.e., non-explosive or non-conductive powder, such as but not limited to: a cobalt chromium molybdenum (CoCrMo) alloy, stainless steel, an austenite nickel-chromium based alloy such as a nickel-chromium-molybdenum-niobium alloy (NiCrMoNb) (e.g., Inconel 625 or Inconel 718), a nickel-chromium-iron-molybdenum alloy (NiCrFeMo) (e.g., Hastelloy® X available from Haynes International, Inc.), or a nickel-chromium-cobalt-molybdenum alloy (NiCrCoMo) (e.g., Haynes 282 available from Haynes International, Inc.), etc.

Processing chamber 130 is filled with an inert gas such as argon or nitrogen and controlled to minimize or eliminate oxygen to, among other things, prevent a reaction with a reactive metal. Control system 104 is configured to control a flow of a gas mixture 160 within processing chamber 130 from a source of inert gas 154. In this case, control system 104 may control a pump 150, and/or a flow valve system 152 for inert gas to control the content of gas mixture 160. Flow valve system 152 may include one or more computer controllable valves, flow sensors, temperature sensors, pressure sensors, etc., capable of precisely controlling flow of the particular gas. Pump 150 may be provided with or without valve system 152. Where pump 150 is omitted, inert gas may simply enter a conduit or manifold prior to introduction to processing chamber 130. Source of inert gas 154 may take the form of any conventional source for the material contained therein, e.g. a tank, reservoir or other source. Any sensors (not shown) required to measure gas mixture 160 may be provided. Gas mixture 160 may be filtered using a filter 170 in a conventional manner.

In operation, metal powder bed 132 is provided within processing chamber 130, and control system 104 controls flow of gas mixture 160 within processing chamber 130 from source of inert gas 154. Control system 104 also controls AM printer 106, and in particular, applicator 140 and lasers 134, 136 to sequentially melt layers of metal powder on metal powder bed 132 to generate object 102.

FIG. 2 shows a cross-sectional view through a selected plane of an intended three-dimensional (3D) model 180 of an illustrative object 102. "Intended 3D model" 180 includes an electronic representation in one of the herein described file formats, e.g., STL or AMF, usable by system 100, of object 102 as it is to be manufactured by system 100. Object 102 may take the form of any object that can be formed by additive manufacturing system 100. For purposes of description, object 102 is assumed to include at least one portion 182 (in phantom ovals) that is subject to thermal defects upon cooling of one or more layers during manufacturing. In the example shown, portion 182 is internal to object 102 and may include, for example, a corner of a cooling channel adjacent to a number of cooling pillars 184. As shown in intended 3D model 102, portion 182 is supposed to be separated from a closest pillar 186. It is emphasized that portion 182 can include any feature, dimension, shape, surface, or other physical attribute of object 102, capable of being deformed during manufacturing compared to intended 3D model 180. Further, portion 182 may be an internal portion and/or an external portion of object 102. Despite the limitations of the two-dimensional drawings, portion 182 may have a three-dimensional extent, i.e., into an out of page.

With reference to FIGS. 3 and 4, a method according to the disclosure is illustrated.

FIG. 3 shows a portion 182M of an object 102M after forming using additive manufacturing system 100 based on intended three-dimensional (3D) model 180 (FIG. 2). Portion 182M of object 102M is supposed to match portion 182 (FIG. 2) of object 102 (FIG. 2) in intended 3D model 180 (FIG. 2). Due to thermal deformation, however, portion 182M includes a thermal defect 188 in the form of an element that bridges from the channel corner to adjacent pillar 186. Conventionally, because such thermal defects are not identifiable by imaging during manufacturing, the only manner to identify such a defect was to destroy object 102M, e.g., by cutting or grinding into the object.

In accordance with embodiments of the disclosure, a tomographic scanner 190 scans at least portion 182M of object 102M to obtain a tomographic scanner model 180M of at least portion 182M of object 102M. Tomographic scanner 190 may include any now known or later developed scanner capable of obtaining a three-dimensional representation, i.e., model, of at least portion 182M of object 102M. Typically, tomographic scanner 190 is separate from additive manufacturing system 100, but in some embodiments, as shown in FIG. 1, may be incorporated as part thereof, e.g., as part of AM printer 106. Tomographic scanner 190 may include any form of device capable of imaging by section(s) using penetrating waves, e.g., x-rays, sound, etc., or capable of creating a 3D image or a 3D point cloud using post-imaging software. Tomographic scanner 190 may include but is not limited to: a phased array ultrasound testing scanner, a coordinate measuring machine, a structured light scanner, a photogrammetry system, and a radiography system (e.g., X-ray). In one preferred example, tomographic scanner 190 may include a computed tomography (CT) scanner such as model number C450, available from GE Inspection Services. In any event, tomographic model 180M includes a three-dimensional representation of at least portion 182M that can be readily electronically sliced along any plane to observe a shape, dimension, etc., thereof, i.e., using conventional scanner display software. As shown in FIG. 3, the scanning process may include rotating (arrows) at least one of: tomographic scanner 190 (all or part thereof) or object 102M, during the scanning. The tomographic scanner format may be any file format typically employed by the chosen scanner, e.g., model C450 from GE, such as Digital Imaging and Communications in Medicine (DICOM) standard format for CT scanners and ultrasound scanners.

The scanner model is converted from the tomographic scanner format into the additive manufacturing system format to obtain a converted tomographic model, also providing a 3D model of object 102M. The additive manufacturing system format that the tomographic scanner format is converted to matches the format of intended 3D model 180, e.g., STL or AMF. The conversion can be performed using any now known or later developed software conversion package, which may be an add-on to the chosen scanner, configured to accommodate the stated conversion. For a CT scanner, for example, the conversion can be carried out using a CT imaging analysis software available from Volume Graphics GmbH of Heidelberg, Germany.

The converted tomographic model 180M is compared to intended 3D model 180 to identify a defect of portion 182M of object 102M. The comparison can include any now known or later developed comparison between 3D models of the same file format, and can be carried out electronically using any now known or later developed software such as that available from Volume Graphics, or can be carried out manually by comparing 3D models.

As shown in FIG. 4, a modified 3D model 180C is generated of the object correcting intended 3D model 180 to address the defect of portion 182M (FIG. 3) of object 102M (FIG. 3). Generating modified 3D model 180C of the object that corrects intended 3D model 180 (FIG. 2) to address the defect may include modifying at least one, but not limited to: a dimension, a surface finish, an overhang quality, and a feature resolution, in intended 3D model 180. In the example shown, portion 182C is re-shaped to be farther away from adjacent pillar 186 to prevent and defect 188 (FIG. 3) from bridging a corner of the channel to adjacent pillar 186. As understood, a variety of alternative modifications could also be applied. The correction can be made by modifying the intended 3D model to that of modified 3D model 180C. The actual correction can be input for control system 104 (FIG. 1) use as a whole new code 1080 (3D model) (FIG. 1) or as a model correction 111 (FIG. 1) for an intended 3D model previously stored as code 1080 (FIG. 1).

Returning to FIG. 2, portion 182 of object 102 may then be formed using additive manufacturing system 102 based on modified 3D model 180C (FIG. 4) of object 102C (FIG. 4). The resulting object would be as shown in FIG. 2, identical to intended 3D model 180.

The teachings of the disclosure may be applied during prototyping of object 102 or after additive manufacturing of object 102. In any event, the method disclosed allows for more accurate modeling and formation of object 102 while addressing thermal defects occurring due to additive manufacturing.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or objects, but do not preclude the presence or addition of one or more other features, integers, steps, operations, elements, objects, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A method, comprising:
    forming a portion of an object using an additive manufacturing system based on an intended three-dimensional (3D) model of the object that is in an additive manufacturing system format;
    scanning the portion of the object using a tomographic scanner to obtain a scanner model of the portion of the object in a tomographic scanner format;
    converting the scanner model from the tomographic scanner format into the additive manufacturing system format to obtain a converted tomographic model;
    comparing the converted tomographic model to the intended 3D model to identify a defect of the portion of the object; and
    generating a modified 3D model of the object correcting the intended 3D model to address the defect of the portion of the object.

2. The method of claim 1, further comprising forming the portion of the object using the additive manufacturing system based on the modified 3D model of the object.

3. The method of claim 1, wherein the portion of the object includes an internal portion of the object, and the converted tomographic model includes a model of the internal portion of the object.

4. The method of claim 1, wherein the tomographic scanner includes a computed tomography (CT) scanner.

5. The method of claim 4, wherein the scanning includes rotating at least one of: the CT scanner or the object, during the scanning.

6. The method of claim 1, wherein the tomographic scanner is selected from the group consisting of: a phased array ultrasound testing scanner, an eddy current scanner, a coordinate measuring machine, a structured light scanner, and a photogrammetry system, and a radiography system.

7. The method of claim 1, wherein the scanner model and the converted tomographic model include three-dimensional models of the portion.

8. The method of claim 1, wherein the additive manufacturing system format is selected from the group consisting of: Standard Tessellation Language (STL) format and Additive Manufacturing File (AMF) format.

9. The method of claim 1, wherein the generating the modified 3D model of the object correcting the intended 3D model to address the defect of the portion of the object includes modifying at least one of the following: a dimension, a surface finish, an overhang quality, and a feature resolution, in the intended 3D model.

10. A method, comprising:
forming a portion of an object using an additive manufacturing system based on an intended three-dimensional (3D) model of the object that is in an additive manufacturing system format;
scanning the portion of the object using a computed tomography (CT) scanner to obtain a CT model of the portion of the object in a CT scanner format;
converting the CT model from the CT scanner format into the additive manufacturing system format to obtain a converted CT model;
comparing the converted CT model to the intended 3D model to identify a defect of the portion of the object; and
generating a modified 3D model of the object correcting the intended 3D model to address the defect of the portion of the object.

11. The method of claim 10, further comprising forming the portion of the object using the additive manufacturing system based on the modified 3D model of the object.

12. The method of claim 10, wherein the portion of the object includes an internal portion of the object, and the CT model includes a model of the internal portion of the object.

13. The method of claim 10, wherein the scanning includes rotating at least one of: an x-ray source of the CT scanner or the object, during the scanning.

14. The method of claim 10, wherein the CT model and the converted CT model include three-dimensional models of the portion.

15. The method of claim 10, wherein the additive manufacturing system format is selected from the group consisting of: Standard Tessellation Language (STL) format and Additive Manufacturing File (AMF) format.

16. The method of claim 10, wherein the generating the modified 3D model of the object correcting the intended 3D model to address the defect of the portion of the object includes modifying at least one of the following: a dimension, a surface finish, an overhang quality, and a feature resolution, in the intended 3D model.

* * * * *